United States Patent [19]

Randin

[11] Patent Number: 5,236,357

[45] Date of Patent: Aug. 17, 1993

[54] INSTRUMENT FOR THE TREATMENT OF ROOT CANALS

[75] Inventor: Jean-Claude Randin, Ballaigues, Switzerland

[73] Assignee: Les Fils D'Auguste Maillefer, Societe Anonyme A Ballaigues, Switzerland

[21] Appl. No.: 896,392

[22] Filed: Jun. 10, 1992

[30] Foreign Application Priority Data

Jun. 26, 1991 [CH] Switzerland .................. 1893/91

[51] Int. Cl.⁵ .............................................. A61C 5/02
[52] U.S. Cl. .................................................... 433/102
[58] Field of Search ................... 433/102, 81, 164, 165

[56] References Cited

U.S. PATENT DOCUMENTS

| | | | |
|---|---|---|---|
| 1,067,015 | 7/1913 | Fowler | 433/102 |
| 1,358,432 | 11/1920 | Fink | 433/165 |
| 3,863,345 | 2/1975 | Malmin | 433/224 |
| 4,205,444 | 6/1980 | Weissman | 433/165 |
| 4,457,710 | 7/1984 | McSpadden | 433/81 |

*Primary Examiner*—Gene Mancene
*Assistant Examiner*—Cindy A. Cherichetti
*Attorney, Agent, or Firm*—Silverman, Cass & Singer, Ltd.

[57] ABSTRACT

A dental instrument has a stem which presents, besides helicoidal ramps providing helicoidal cutting edges, annular grooves of V-shaped cross-section and spaced apart. One of the faces of each of the grooves is perpendicular to the longitudinal axis of the instrument. Due to the grooves, the instrument can be used not only as a reamer, with a rotative movement, but also as a file, with a back and forth movement when the faces of the grooves produce a scraping effect on the wall of the root canal being treated.

6 Claims, 1 Drawing Sheet

INSTRUMENT FOR THE TREATMENT OF ROOT CANALS

BACKGROUND OF THE INVENTION a) Field of the Invention

The present invention relates to an instrument for use in dentistry, such as a reamer or a file, serving for the treatment of root canals and comprising a tapered stem presenting at least a helicoidal cutting edge.

b) Description of the Prior Art

The difference between dental reamers and the files lies in the fact that the latter are used with a back and forth movement, as their name suggests, while the former are supposed to be used in the manner of drills, with a rotative movement, with the difference, however, that drills usually effect a continuous unidirectional rotative movement while, in the case of a reamer for the treatment of root canals, the practitioner manually imparts only fractions of revolutions to the instrument and withdraws the latter with the waste produced by the operation between each rotation.

However, it appears that in practice the practitioners, frequently use the reamers as if they were files, that is to say by imparting thereto a back and forth movement, even by combining such a back and forth movement with a rotative movement.

Taking into account the foregoing fact, it appears that it would be advantageous to procure that this irregular use of the reamers be efficiently utilized. The present invention has for an object to provide this advantage.

Moreover, if not applied to reamers but instead to files, the invention also improves the efficiency of the latter. Consequently, it has a favorable effect in both cases.

SUMMARY OF THE INVENTION

An instrument according to the invention comprises a series of annular grooves, spaced from each other and effective to remove root material when a back and forth longitudinal movement is imparted to the instrument.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be used and structural changes may be made as desired by those skilled in the art without departing from the present invention and the purview of the appended claims.

DESCRIPTION OF THE PREFERRED EMBODIMENTS

Figure 1:
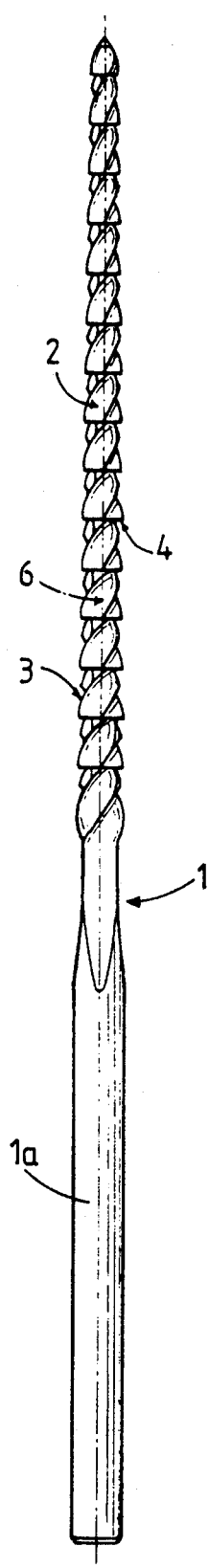
FIG. 1 is an elevational view, to an enlarged scale of 10:1, of a reamer in accordance with the invention for the treatment of dental root canals.
Figure 2:
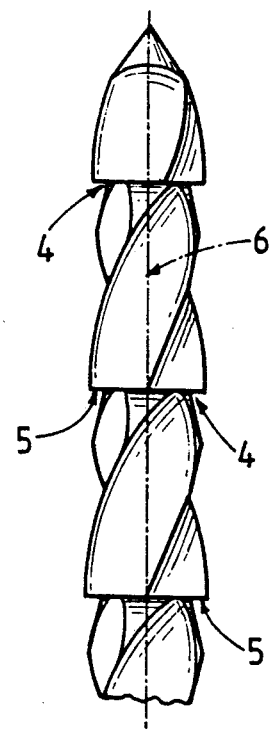
FIG. 2 is an elevational view of the leading portion of this instrument, to a four times greater scale.

The instrument illustrated in FIGS. 1 and 2 comprises a tapered stem 1 presenting four helicoidal ramps 2 providing four helicoidal cutting edges 3.

This instrument is made starting from a round stem a major portion of the length of which is tapered, working the stem in order to give it a square cross-section, and then submitted the stem to a torsional deformation thus producing the helicoidal ramps 2. The rear portion of the stem 1, designated by reference 1a, remains of circular section and constitutes the handle of the instrument. It could be of a larger cross-section than is the case in the example illustrated and be milled so that it is more easily gripped and thus facilitating utilization of the instrument by the dental practitioner who will grip the said handle between thumb and index finger.

The instrument as illustrated presents moreover a series of annular grooves 4, of V-shaped cross section, obtained by working, regularly distributed along the tapered portion of the stem 1. One of the faces of each groove 4, designated by reference 5, is perpendicular to the longitudinal axis of the instrument, indicated at 6.

Owing to the presence of the grooves 4, the reamer can be used as a file with a back and forth movement during which, as the instrument is pulled back, the grooves 4 effect a scraping of the wall of the root canal with removal of material.

Figure 3:
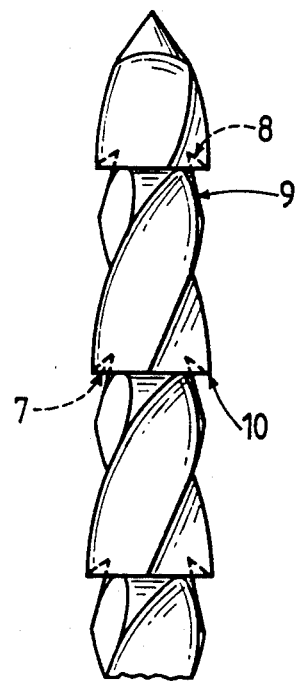
FIGS. 3 and 4 are elevational views of two modifications, similar to that of FIG. 2 and to the same scale.

The modification of FIG. 3 distinguishes from the first embodiment by the fact that the annular grooves, now designated by reference 7, have their two faces, respectively designated by references 8 and 9, both inclined with respect to the longitudinal axis of the instrument. They are mutually inclined at an acute angle, in such a way that the annular lip produced by each groove, indicated by reference 10 in FIG. 3, presents a sharp edge which is more aggressive in the cutting sense than is the case with the embodiment of FIGS. 1 and 2.

Figure 4:
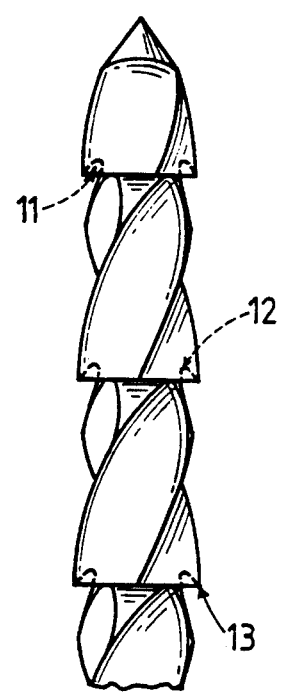

FIG. 4 shows a modification which is closer to that of FIG. 3, with the difference that the annular grooves, now designated by reference 11, present a rounded bottom constituted by a concave surface of revolution 12, thus again providing an annular cutting edge 13.

The invention is not limited to the type of instrument illustrated in the drawings. It could be applied to instruments for the treatment of root canals comprising less than four helicoidal cutting edges, to instruments the cutting edges of which will be more or less close to each other than in the examples described to instruments presenting crossed cutting edges, that is to say with some effective rotating clockwise and the others effective rotating counter-clockwise or also to instruments the angle of the conicity of which will go increasing from the leading point of the instrument in the direction of the handle so that the active portion thereof present some concavity.

At least, one could provide that the instrument does not present annular grooves on its whole length, but only on a portion of the length, or in which these grooves are not equally spaced from each other but, for example, in which the spacing between them increases from the leading end of the instrument in the direction of the handle.

I claim:

1. An instrument for use in dentistry, such as a reamer or a file, for the treatment of root canals, said instrument comprising, a tapered stem presenting at least one helicoidal cutting edge, a series of annular grooves which are spaced from each other along the stem, each of said annular grooves intersecting said cutting edge and operable to remove root material when a back and forth longitudinal movement is applied to the instrument.

2. An instrument as claimed in claim 1, in which said grooves are V-shaped cross-section.

3. An instrument as claimed in claim 2, in which one of the faces of each of said grooves is situated in a plane which is perpendicular to the longitudinal axis of the instrument.

4. An instrument as claimed in claim 2, in which the two faces of said grooves are frusto-conical, the angle between their generatrix being an acute angle.

5. An instrument as claimed in claim 2, in which the bottom of each of said grooves is rounded.

6. An instrument as claimed in claim 1, in which said grooves are distributed along the stem of the instrument at unequal spacings from each other, the spacing which separates two neighbouring grooves increasing from the leading end of the instrument in the direction of a handle of the instrument.

* * * * *